(12) United States Patent
Lockart

(10) Patent No.: US 10,966,854 B1
(45) Date of Patent: Apr. 6, 2021

(54) BRACE WITH A VARIABLE RESISTANCE BAND SYSTEM

(71) Applicant: Brice W Lockart, Tallahassee, FL (US)

(72) Inventor: Brice W Lockart, Tallahassee, FL (US)

( * ) Notice: Subject to any disclaimer, the term of this patent is extended or adjusted under 35 U.S.C. 154(b) by 96 days.

(21) Appl. No.: 16/560,616

(22) Filed: Sep. 4, 2019

(51) Int. Cl.
*A61F 5/01* (2006.01)
*A63B 21/04* (2006.01)

(52) U.S. Cl.
CPC ............ *A61F 5/0123* (2013.01); *A61F 5/013* (2013.01); *A63B 21/0407* (2013.01); *A61F 2005/0139* (2013.01); *A61F 2005/0153* (2013.01)

(58) Field of Classification Search
CPC .......... A61F 5/0123; A61F 5/01; A61F 5/013; A61F 5/0102; A61F 2005/0139; A61F 2005/0153; A61F 2005/0179; A61F 2005/0137; A61F 2005/0167; A61F 2005/0132; A61F 2005/0144; A61F 2005/0146; A61F 2/64; E05D 3/122; F16H 19/04; F16H 55/26; A63B 21/0407; A63B 21/4025
See application file for complete search history.

(56) References Cited

U.S. PATENT DOCUMENTS

| | | | |
|---|---|---|---|
| 4,606,542 A * | 8/1986 | Segal | A61F 5/0125 |
| | | | 482/105 |
| 5,167,612 A * | 12/1992 | Bonutti | A61F 5/0123 |
| | | | 601/33 |
| 5,203,754 A | 4/1993 | Maclean | |
| 5,213,094 A * | 5/1993 | Bonutti | A61F 5/0123 |
| | | | 601/33 |
| 5,356,370 A * | 10/1994 | Fleming | A61F 5/0123 |
| | | | 403/158 |
| 5,685,830 A | 11/1997 | Bonutti | |
| 5,865,714 A | 2/1999 | Marlowe | |
| 6,063,048 A | 5/2000 | Bodenschatz et al. | |
| 6,537,237 B1 | 3/2003 | Hopkins et al. | |
| 7,048,704 B2 | 5/2006 | Sieller et al. | |
| 7,156,819 B2 | 1/2007 | Sieller et al. | |
| 7,553,289 B2 * | 6/2009 | Cadichon | A61F 5/0123 |
| | | | 602/23 |
| 7,608,051 B1 | 10/2009 | Nace | |
| 7,963,933 B2 | 6/2011 | Nace | |
| 8,057,414 B2 | 11/2011 | Nace | |
| 8,308,669 B2 | 11/2012 | Nace | |
| 8,376,974 B2 | 2/2013 | Nace | |

(Continued)

*Primary Examiner* — Victoria J Hicks
*Assistant Examiner* — Kevin S Albers
(74) *Attorney, Agent, or Firm* — Peter Loffler

(57) ABSTRACT

A brace assists a user in regaining muscle mass during the back to work phase of joint injury recovery. The brace uses a resistance band that is attached to the upper arm and the lower arm of the brace. Proximate the arms' juncture point, a pair of gears is attached, one gear per arm with a gap between the gears. The gears rotate in lockstep with their respective arm. A variation piece has two sets of teeth, each set gearably mating with one of the gears so that rotation of the gears causes the variation piece to linearly extend and counter-rotation causes the variation piece to retract. A medial portion of the band is received by the variation piece so that as variation piece extends, it places additional tension on the band, which tension placement is reduced with variation piece retraction.

12 Claims, 9 Drawing Sheets

(56) References Cited

U.S. PATENT DOCUMENTS

| | | | |
|---|---|---|---|
| 8,882,688 B1* | 11/2014 | Ancinec | A61F 5/0125 |
| | | | 602/16 |
| 9,114,277 B2 | 8/2015 | Goeckel | |
| 9,220,623 B2 | 12/2015 | Burns | |
| 9,452,075 B2 | 9/2016 | Berg | |
| 9,844,454 B2* | 12/2017 | Garrish | A61F 5/013 |
| 10,085,869 B2* | 10/2018 | Nace | A61F 5/012 |
| 2005/0192522 A1* | 9/2005 | Houser | A61F 5/0123 |
| | | | 602/16 |
| 2007/0094846 A1* | 5/2007 | Ishida | E05D 15/264 |
| | | | 16/354 |
| 2011/0105969 A1 | 5/2011 | Nace | |
| 2011/0207585 A1* | 8/2011 | Burns | A61F 5/0123 |
| | | | 482/124 |
| 2013/0110020 A1 | 5/2013 | Ingimundarson et al. | |
| 2017/0071775 A1* | 3/2017 | Garrish | A61F 5/0102 |

\* cited by examiner

BRACE WITH A VARIABLE RESISTANCE BAND SYSTEM

BACKGROUND OF THE INVENTION

1. Field of the Invention

The present invention relates to a competition brace, such as a knee brace or elbow brace, that has a removable variable resistance band system attached to the brace in order to assist a patient who has undergone a knee procedure or otherwise suffered a knee injury in regaining extension and hyperextension flexibility as well as assist the patient in regaining lost muscle mass in the muscles about the joint.

2. Background of the Prior Art

When a patient has a knee procedure performed, the patient is fitted with a brace immediately thereafter in order to keep the operated upon knee and/or limb from being injured. A typical knee brace comprises an upper sleeve that encircles the patient's leg above the knee and a lower sleeve that encircles the patient's leg below the knee. A hinge system comprising one or more hinges connects the upper sleeve with the lower sleeve and allows articulation between the two sleeves about the knee. The hinges are placed on opposing lateral (side) portions of the knee brace. The knee brace protects the patient by limiting the joint range of motion through a locking system at variable degrees, as prescribed by their physician relative, during their progression in the rehabilitation process. The locking system is part of the hinge system. The current brace models provide a range of motion anywhere from about –10 degrees (hyperextension) to about 120 degrees of flexion. Elbow braces are structured similarly and function in similar fashion.

These knee braces tend to be relatively bulky and are used to protect the repaired area and are often referred to as repair phase braces. These repair phase braces are worn during the initial post-surgery rehabilitation phase of the overall joint repair. Once the patient progresses beyond this initial period, the patient is switched to a competition or return to work brace which helps the patient transition from the relatively restrictive repair brace to a more streamlined and less bulky brace that gives the patient greater range of motion.

While wearing the competition brace, the patient intensifies their physical rehabilitation process in order to get back to (or as near as possible) the condition the joint was in prior to the injury that necessitated the repair. Patients are often cleared to perform resistance training while wearing the competition brace in order to reverse the muscle atrophy that has occurred since the injury. Even with such clearance, the patient must be closely monitored in order to avoid causing any shearing or other damage to the freshly repaired joint, which shearing or other injury could necessitate another repair procedure. As such, the patient is limited in what types of resistance training can be performed. Often, a patient engages in open-chain kinetic resistance training and avoids closed-chain resistance training. Open-chain resistance training does a great job of isolating the muscles around the joint, but force the upper portion of the limb above the joint to be fixated against a seat or pad. The machine then applies resistance to the most distal point of the lower limb away from the pivot point of the joint (typically the hand or ankle). Even with careful monitoring, this type of exercising can still cause a significant sheer effect on the joint. Other resistance training methods are available, but are extremely low impact and non-invasive in comparison to the open-chain machines, thus requiring a significantly longer amount of time to regain the atrophied muscle and often more costly as the patient needs to attend physical therapy sessions to perform such techniques.

What is needed is a device that assists a patient that has undergone a knee procedure in the return to work or competition phase of rehabilitation which addresses the above stated shortcomings found in the art. Such, a device must be able to assist the patient in regaining leg muscle mass that may have been lost to atrophy post-surgery (and possibly pre-surgery). Such a device must minimize the risk of injury to the patient during device usage. Such a device should be able to perform its task while the patient performs ordinary tasks so as to eliminate the burden of having to attend rehabilitation specific sessions to achieve the desired results.

SUMMARY OF THE INVENTION

The brace with variable resistance band system of the present invention addresses the aforementioned needs in the art by providing a competition knee brace that offers structural support development of the surrounding muscle groups of the knee joint (or elbow joint) through greater resistive loading to help facilitate the patient's efforts in transitioning from joint rehabilitation to returning to play/competition use of the joint. This makes the brace with variable resistance band system into an extensive portable rehabilitation tool that offers a safer and faster rehabilitation experience to a surgically repaired joint while reducing the potential for anterior/posterior sheer effect on the knee/joint, compared to conventional rehab methods of open-chained kinetic resistance training. The brace with variable resistance band system uses variably quantifiable resistance tools to assist the joint in hyperextension as the patient is walking, during flexion of the knee, by loading the hamstring as well as during extension of the knee, by loading the quadriceps—the brace also provides loading and resistance while the wearer is running if the user is so cleared. The brace with variable resistance band system creates static tension/resistance to help hyperextend the joint while the brace is on the limb and the restriction pins are removed. The majority of the brace with variable resistance band system is quickly and easily removable from the brace proper so that the brace can be utilized in normal fashion without the system attached, this being especially helpful when the brace is worn underneath clothing. The brace with variable resistance band system reduces anterior/posterior sheer effect on the knee/joint, compared to conventional rehab methods of open-chained kinetic resistance training. By reducing or even eliminating the need to attend physical therapy sessions related to muscle atrophy reversal, the brace with variable resistance band system reduces the impingement on the patient's time and financial resources. The brace with variable resistance band system can be used on healthy limbs during sprint conditioning and similar types of events. The brace with variable resistance band system is of relatively simple design and construction, being produced using standard manufacturing techniques, so as to make the device readily affordable to potential consumers for this type of system. The resistance band used with the knee brace is readily attachable to and detachable from the knee brace as is the pivot mechanism that affords the resistance of a given band to be variable so that the majority of the system is easily donned when needed and doffed when not desired, allowing the brace to be used in conventional fashion as well as allowing for rapid change of resistance of the system.

The brace with variable resistance band system of the present invention is comprised of a competition or return to work brace that has an upper arm pivotally attached to a hinge plate and a lower arm also pivotally attached to the hinge plate and gearably mated with the upper arm. Rotation of the upper arm causes the lower arm to counter-rotate in lockstep and vice versa. A first gear is attached to the upper arm such that the first gear rotates in lockstep with rotation of the upper arm. A second gear is attached to the lower arm such that the second gear rotates in lockstep with rotation of the lower arm. A variation piece has a head and a stem. The stem has a first set of teeth that mesh with the first gear and a second set of teeth that mesh with the second gear. Rotation of the first gear and the second gear causes the variation piece to linearly travel in a first direction and counter-rotation of the first gear and the second gear causes the variation piece to linearly travel in a second opposing direction. A first resistance band has a first end attached to the upper arm of the brace and a second end attached to the lower arm and a medial section received by the head of the variation piece. A top plate is attached to the hinge plate such that the upper arm, lower arm, first gear and second gear are sandwiched between the top plate and the hinge plate. The medial section of the first resistance band is received within a channel located on the head of the variation piece. An alignment means is provided for assisting the variation piece in staying aligned in its linear travel. The alignment means may comprise a screw that passes between the top plate and the hinge plate and a cutaway that is located on the stem of the variation piece between the first set of teeth and the second set of teeth such that the screw is received within the cutaway and can travel therein. Alternately, or in addition, a rail is located on the top plate such that at least a portion of the rail is received within the cutaway. Alternately, or in addition, the alignment means can comprise a rectangular base that forms a part of the stem such that the first set of teeth and the second set of teeth sit on the rectangular base and a channel is formed within the top plate such that at least a portion of the rectangular base is received within the channel and slides therein. A second resistance band has a third end attached to the upper arm of the brace on a side opposite the attachment of the first resistance band and a fourth end attached to the lower arm on a side opposite the attachment of the first resistance band.

BRIEF DESCRIPTION OF THE DRAWINGS

Similar reference numerals refer to similar parts throughout the several views of the drawings.

DESCRIPTION OF THE PREFERRED EMBODIMENT

Figure 1:
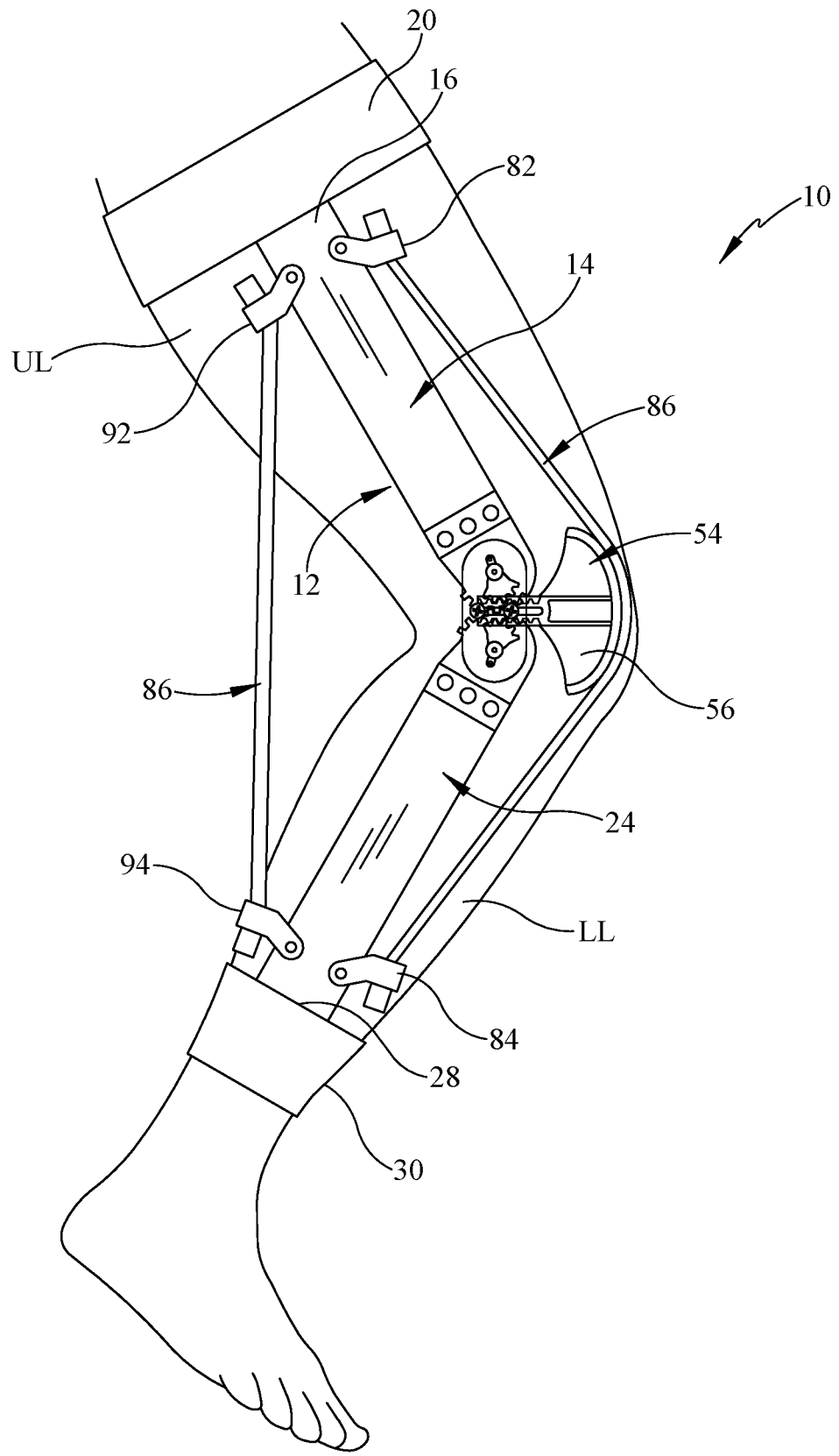
FIG. 1 is an environmental view of the brace with variable resistance band system of the present invention with the resistance band being forward located and a user's knee being bent.

Referring now to the drawings, it is seen that the brace with variable resistance band system of the present invention, generally denoted by reference numeral 10, is comprised of a competition knee brace 12 (or elbow brace) of any convention type. As seen, the typical brace 12 has an upper arm 14 with an upper top 16 and an upper bottom 18. An upper sleeve 20 is located proximate the upper top 16. The upper sleeve 20 encircles a portion of the user's upper limb UL and is secured thereat in appropriate fashion. As seen, upper arm teeth 22 are located on the upper bottom 18 of the upper arm 14. The brace 12 also has a lower arm 24 with a lower top 26 and a lower bottom 28. A lower sleeve system 30 encircles a portion of the user's lower limb LL and is secured thereat in appropriate fashion. As seen, lower arm teeth 32 are located on lower top 26 of the lower arm 24. Appropriate sizing means may be located on each sleeve system 20 and 30 in order to assure a snug fit of the respective sleeve system about the respective portion of the user's limb.

A hinge system 34 connects the upper arm 14 and the lower arm 24. As seen, the hinge system 34 comprises a hinge plate 36 wherein an upper pivot pin 38 passes through the upper arm 14 and the hinge plate 36 so that the upper arm 14 is secured to the hinge plate 36 and is able to pivot with respect to the hinge plate 36. Similarly, a lower pivot pin 40 passes through the lower arm 24 and the hinge plate 36 so that the lower arm 24 is secured to the hinge plate 36 and is able to pivot with respect to the hinge plate 36. When the upper arm 14 and the lower 24 are attached to one another, the upper arm teeth 22 and the lower arm teeth 32 are gearably meshed with one another so that each arm 14 and 24 pivots with respect to the hinge plate 36 in counter-rotation lockstep with the other arm 24 and 14. Typical restriction pins (not illustrated) can be used with the brace 12 as is known in the art.

As seen, the upper pivot pin 38 also passes through an upper gear 42 that has upper gear teeth 44. An upper securement pin 46 passes through the upper gear 42 so that the upper gear 42 is fixedly secured to the upper arm 14 so that the two pivot with respect to the hinge plate 36 together. Similarly, the lower pivot pin 40 also passes through a lower gear 48 that has lower gear teeth 50. A lower securement pin 52 passes through the lower gear 48 so that the lower gear 48 is fixedly secured to the lower arm 24 so that the two pivot with respect to the hinge plate 36 together. As seen, a gap exists between the upper gear teeth 44 and the lower gear teeth 50 when they face one another.

Figure 2:
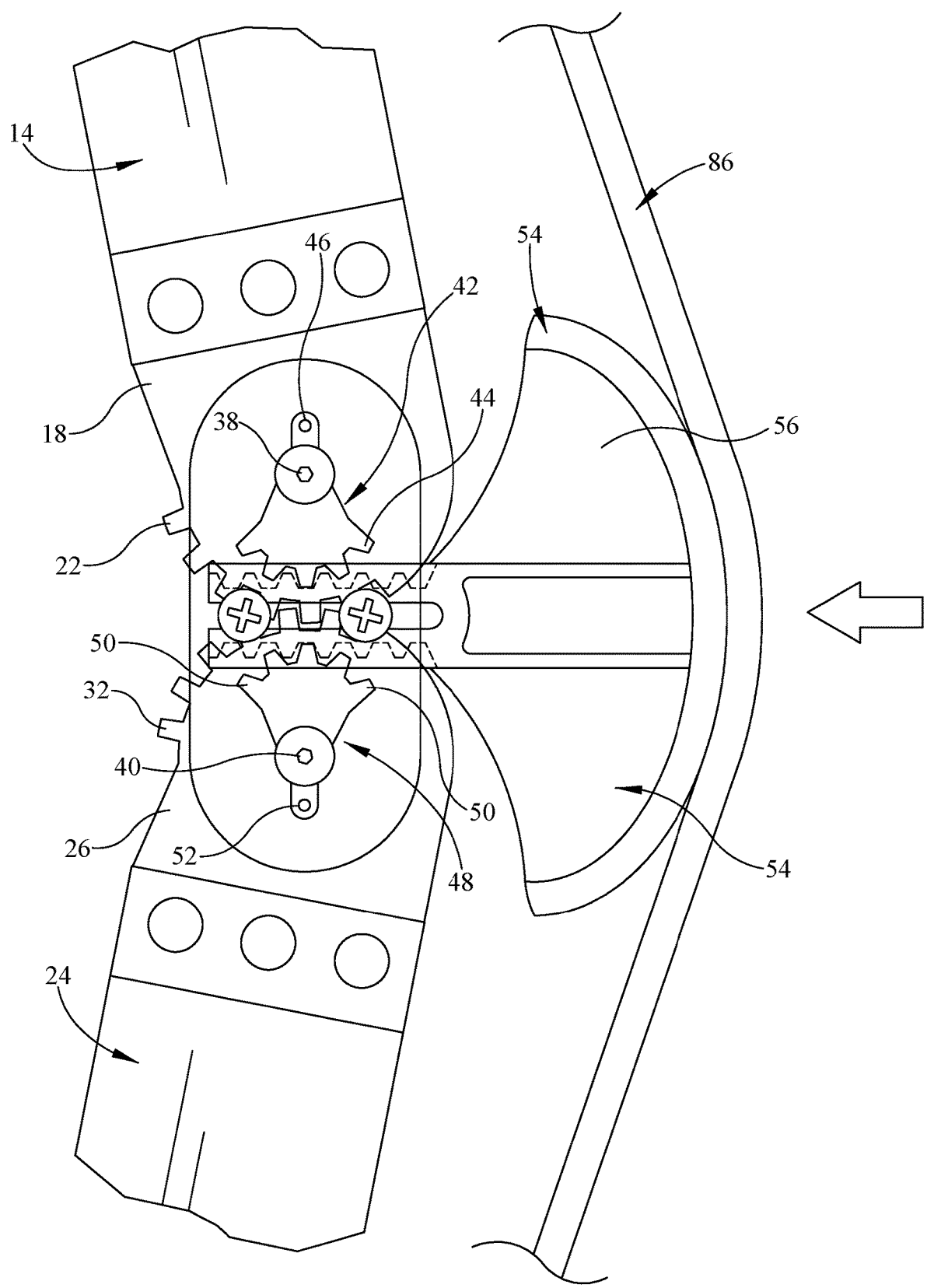
FIG. 2 is a close-up elevation view of the brace with variable resistance band system with a slight bend of the brace.
Figure 3:
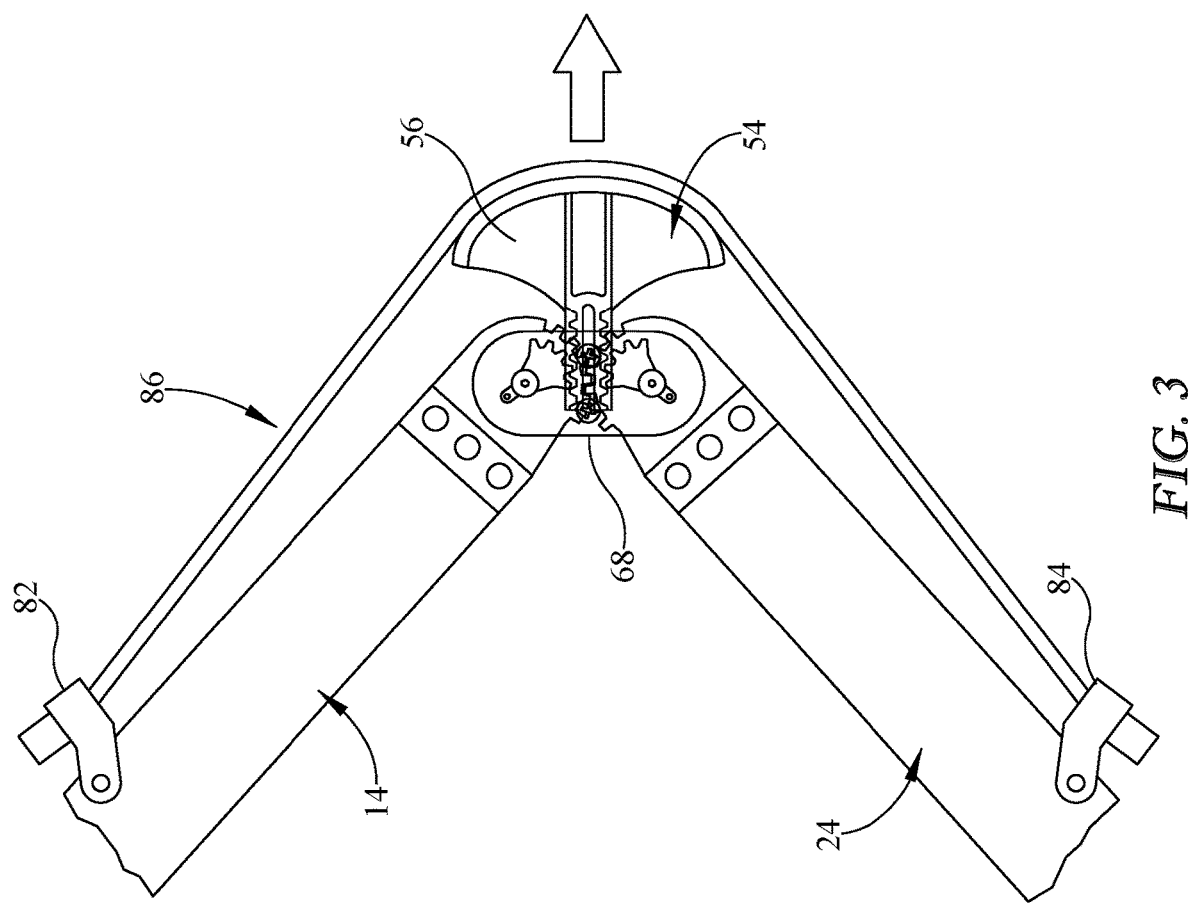
FIG. 3 is an elevation view of the brace with variable resistance band system with a significant bend of the brace.
Figure 4:
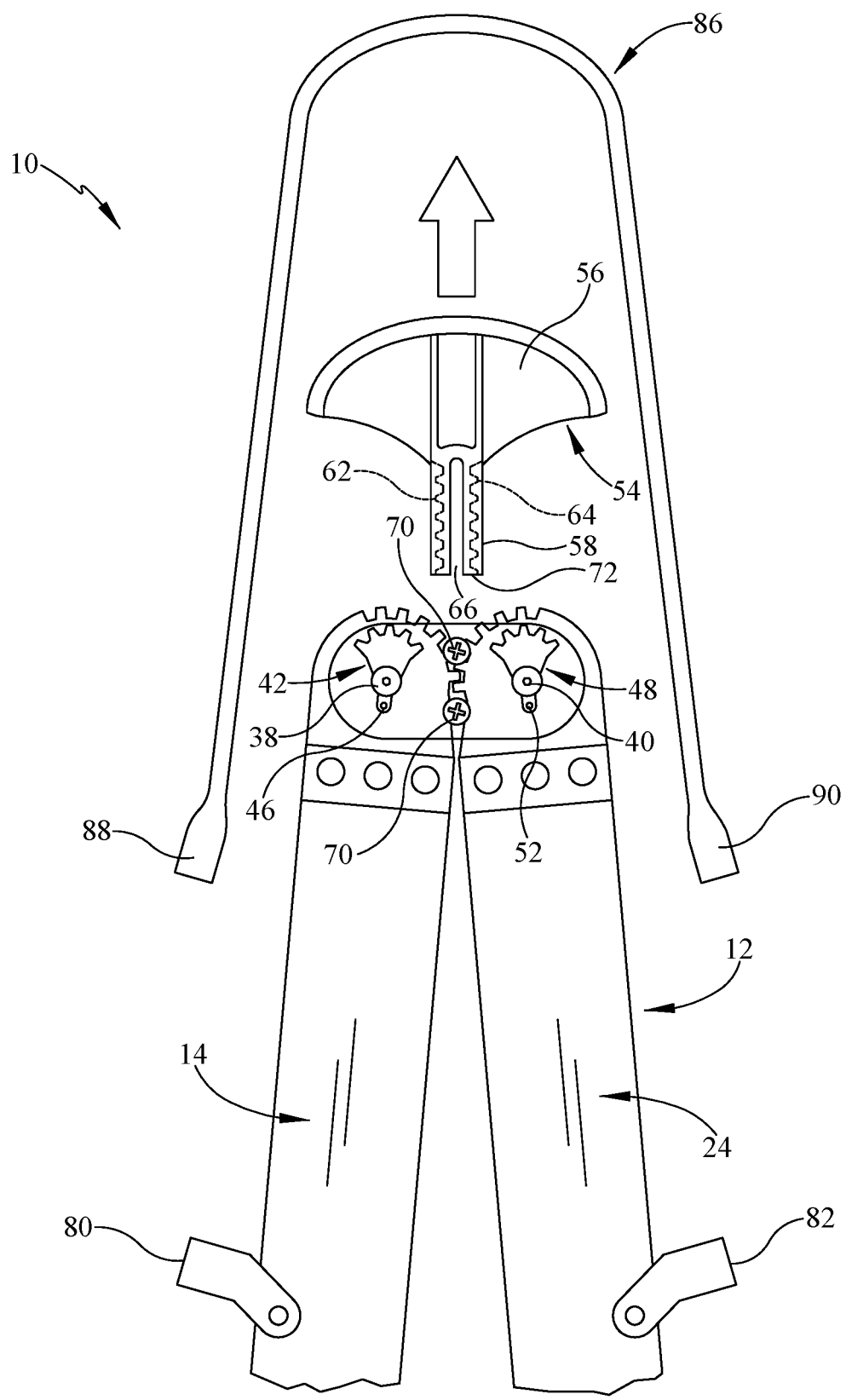
FIG. 4 is an elevation view of the brace with variable resistance band system being disassembled.
Figure 5:
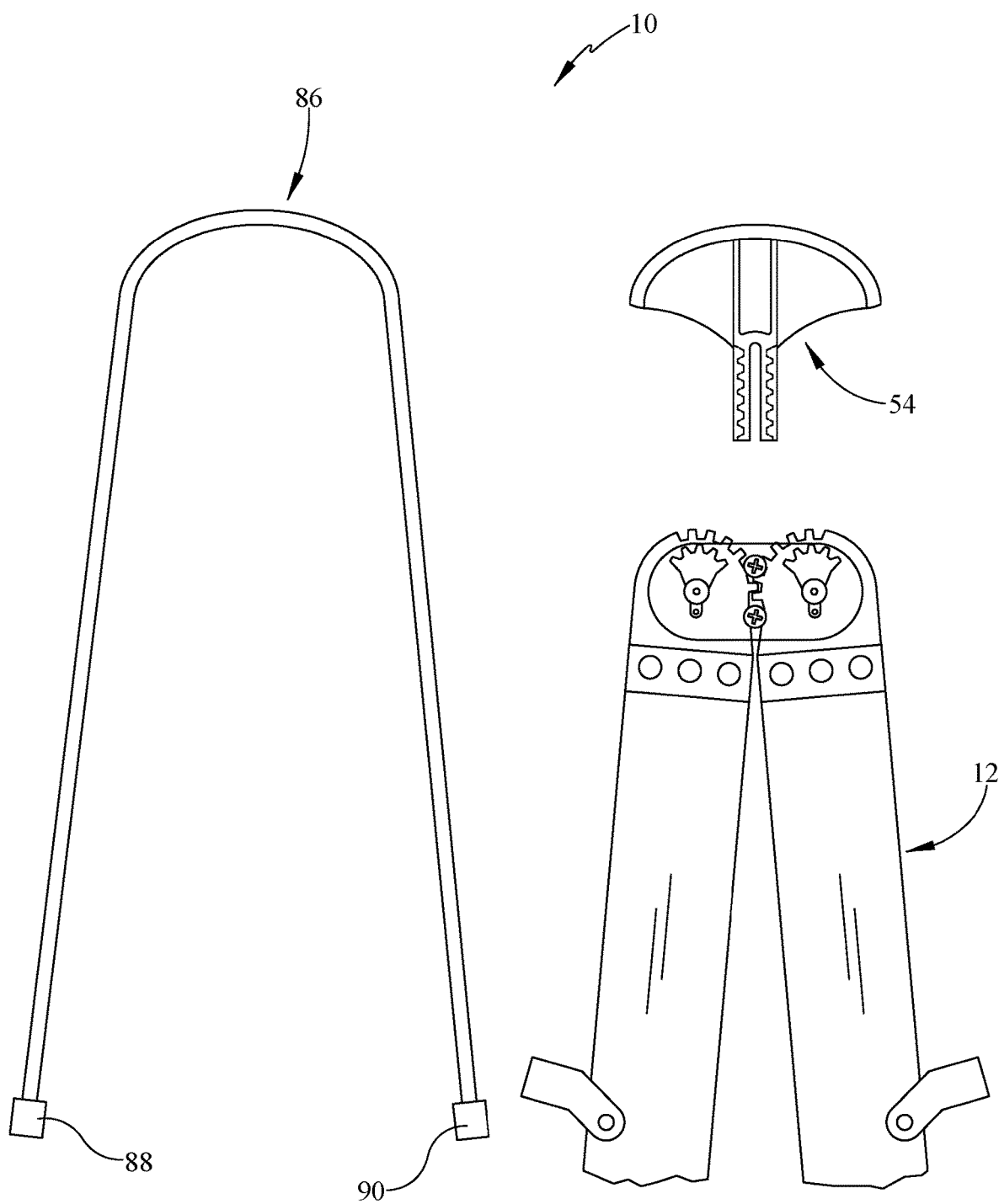
FIG. 5 is an elevation view of the brace with variable resistance band system fully disassembled.
Figure 6:
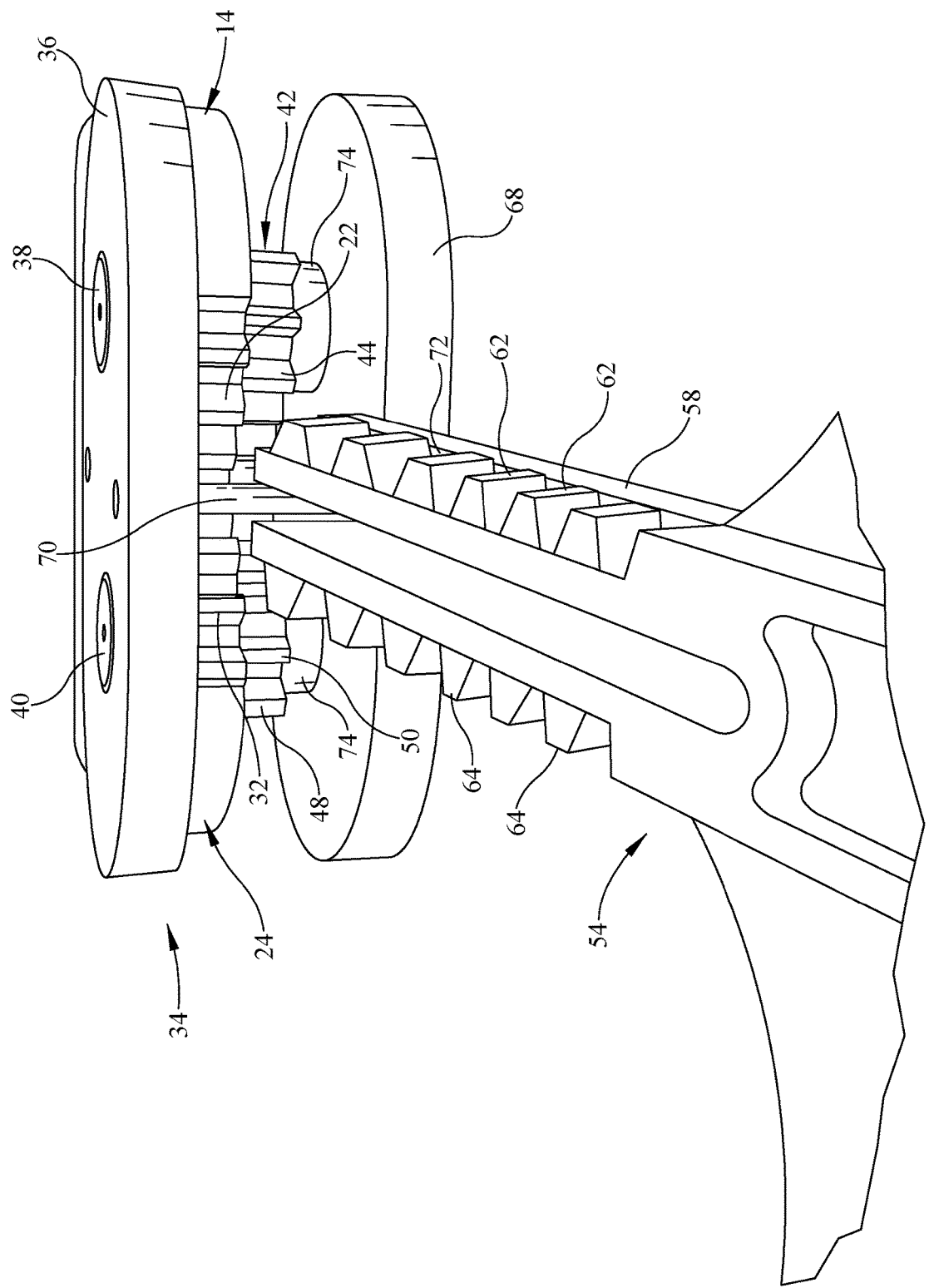
FIG. 6 is a perspective view of the brace with variable resistance band system illustrating the gearing mechanism of the system.

A variation piece 54 has a rounded head 56 and a stem 58 depending downwardly therefrom. The outer portion of the head 56 is rounded and has a curved channel 60. The stem 58 has a first set of stem teeth 62 along one side facing outwardly and a second set of stem teeth 64 along the other side also facing outwardly—the two sets of stem teeth 62 and 64 face away from one another. A central cutaway 66 extends from a bottom of the stem 58 toward the head 56. A top plate 68 is attached to the system by positioning the top plate 68 over the upper gear 42 and lower gear 48 and securing the top plate 68 to the hinge plate 36 via the upper pivot pin 38 and the lower pivot pin 40. A pair of screws 70 is also passed through the two plates 36 and 68 in order to help with variation piece 54 linear travel alignment. The variation piece 54 is attached to the brace 12 by inserting the stem 58 between the upper gear 42 and the lower gear 48 which can be accomplished when the brace 12 is fully flexed as seen in FIGS. 4 and 5—upper top 16 brought toward the lower bottom 28. As the brace 12 is pivoted out of full flexion, the upper gear teeth 44 of the upper gear 42 mesh with the first set of stem teeth 62 while simultaneously, the lower gear teeth 50 of the lower gear 48 mesh with second set of stem teeth 64 and gearably move the variation piece 54 into a retracted position as best seen in FIG. 2. Counter-rotation of the upper arm 14 and lower arm 24 moves the variation piece 54 into an extended position as seen in FIG. 3. The first set of stem teeth 62 and the second set of stem teeth 64 are always engaged with the respective gear teeth 44 and 50 except when the brace 12 is fully flexed as described previously. The screws 70 are received within the cutaway 66 of the stem 58 so as to not impede up and down travel of the variation piece 54 and also to help keep the variation piece aligned and not listed to one side or another.

The stem 58 of the variation piece 54 may have its stem teeth 62 and 64 fully cut away instead of being inset on a rectangular base 72 as shown (the teeth form the entire outer edge of the respective sides of the stem), however, the inset design allows the use of risers 74 located between the upper plate 68 and the upper gear 42 (upper pivot pin 38 and lower pivot pin 40 each passing through a respective one of the risers 74) and lower gear 48 which risers 74 help give the variation piece 54 smooth and stable travels within the system. The risers 74 may be an integral part of the upper plate 68 or the respective pivot pins 38 and 40, or may be separate items.

Figure 7:
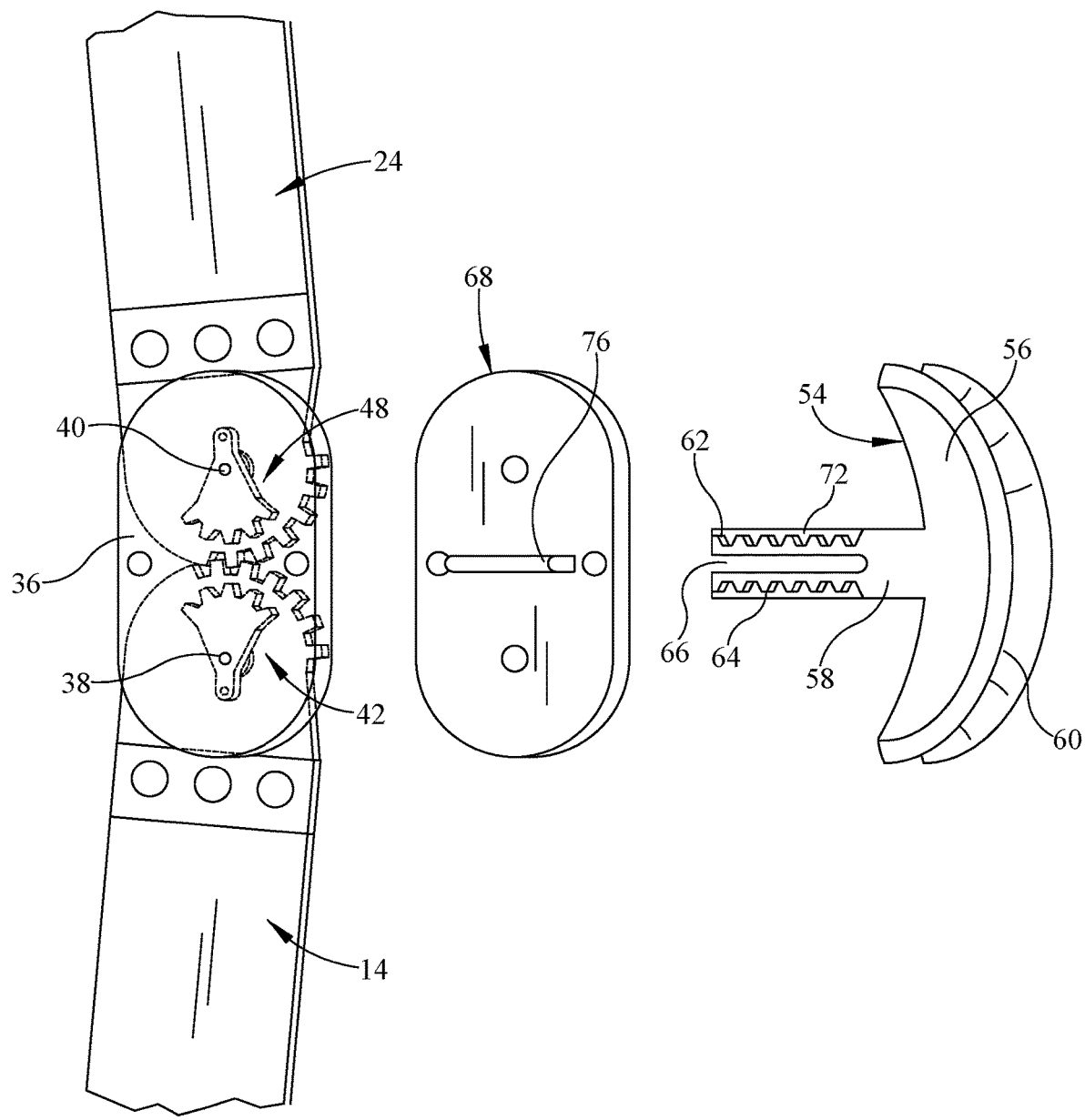
FIG. 7 is a perspective view of the brace with variable resistance band system disassembled and illustrating an optional guide rail.

Additionally, as seen in FIG. 7, a rail 76 may be located on the inside facing surface of the top plate 68 so that the rail 76 is received within the cutaway 66 of the stem 58 to assist the screws 70 in keeping the variation piece 54 aligned (when the variation piece 54 is at or near its extended position, only one of the screws 70 is within the cutaway 60 giving the variation piece 54 the opportunity to pivot out of alignment. The rail 76 maintains alignment of the variation piece 54 even if the screws 70 are not deployed.

Figure 8:
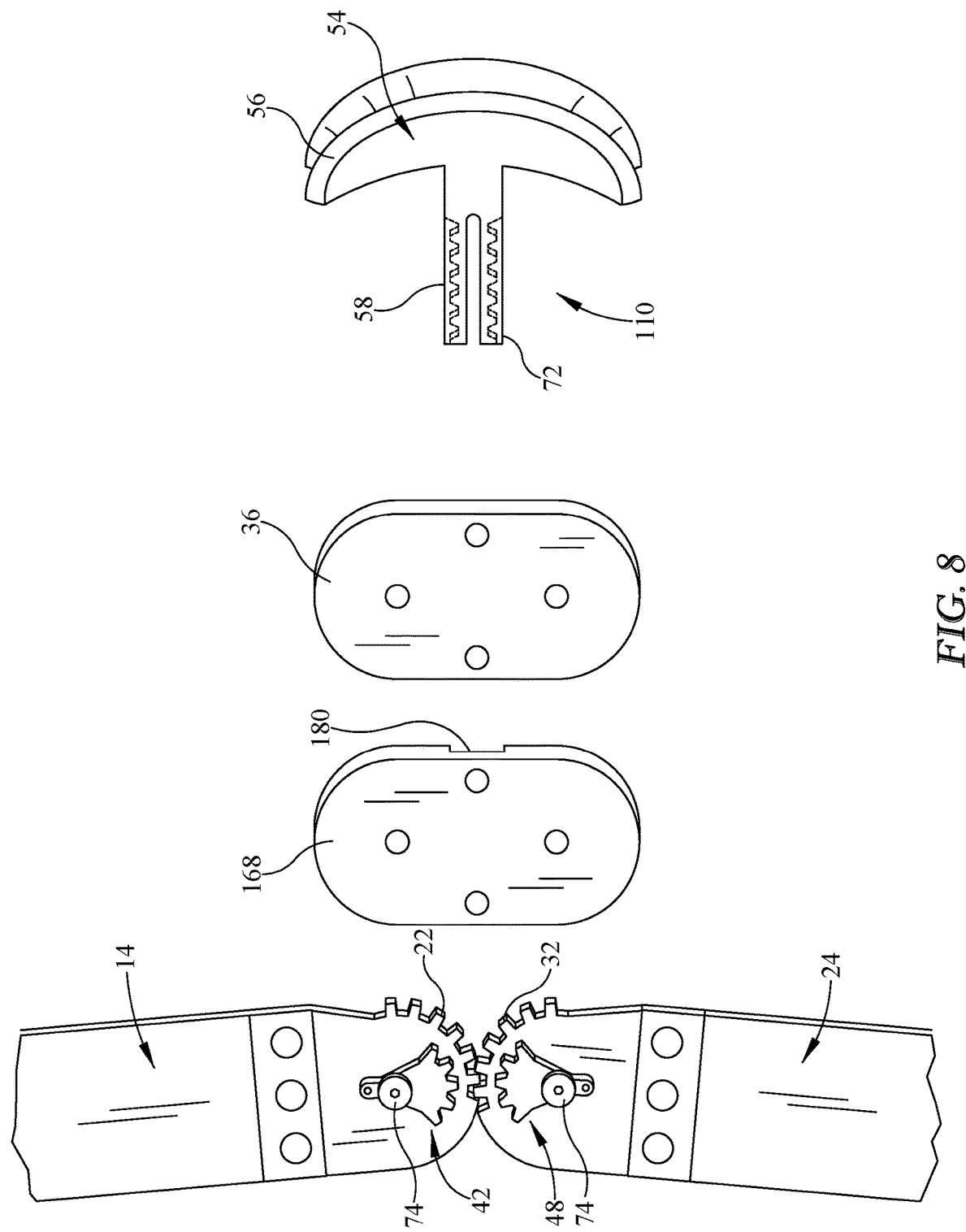
FIG. 8 is a perspective view of an alternate embodiment, disassembled, of the brace with variable resistance band system of the present invention.
Figure 9:
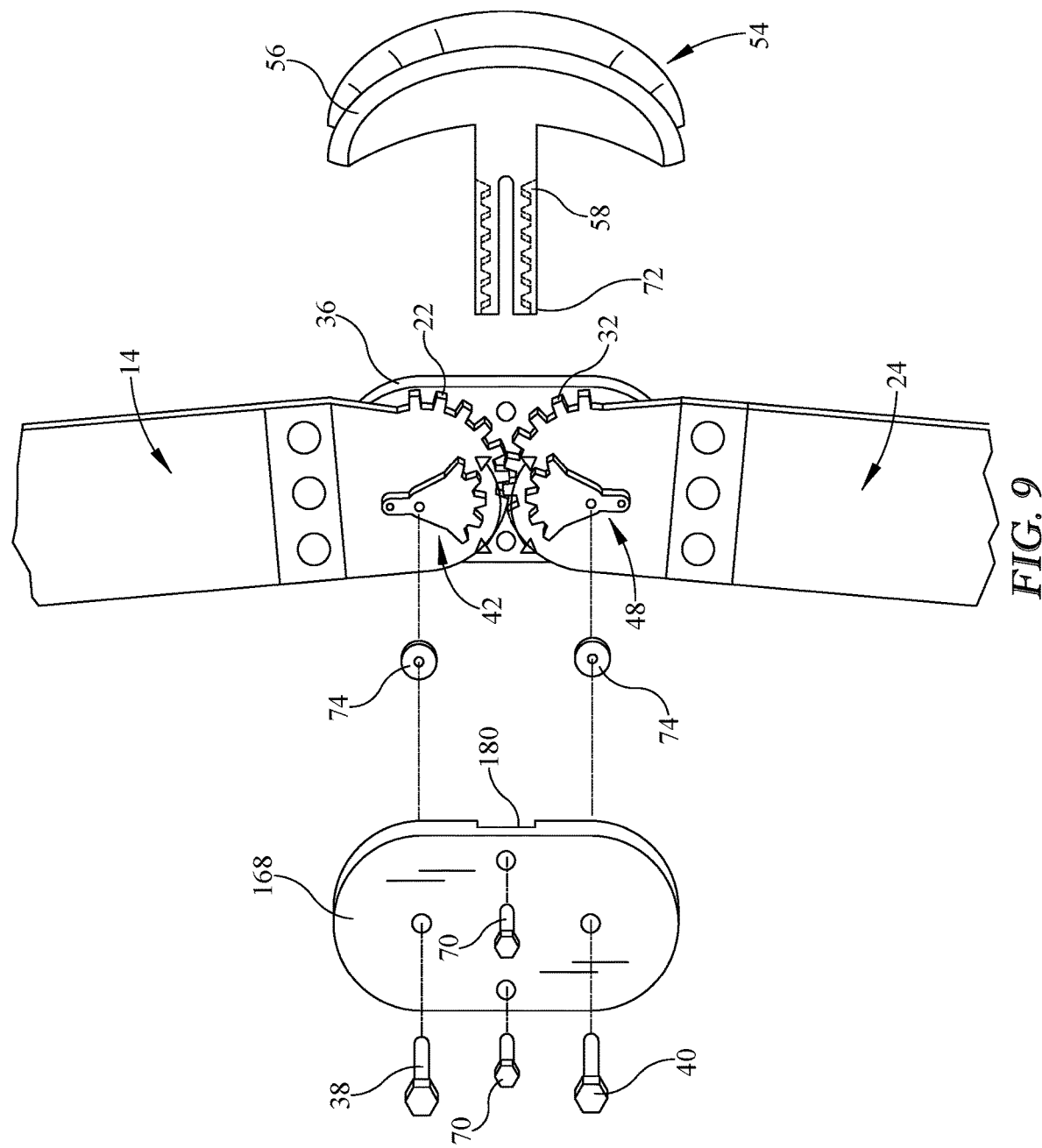
FIG. 9 is an exploded perspective view of the brace with variable resistance band system of FIG. 8.

As seen in FIGS. 8 and 9, in an alternate embodiment of the brace with variable resistance band system 110 of the present invention, the top plate 168 has a plate channel 180 extending down a midline of the inside facing surface of the top plate 168. When the variation piece 54 is inserted into the top plate 168-hinge plate 36 sandwich, the rectangular base 72 of the stem 58 of the variation piece 54 fits snugly within the plate channel 180 and slides therein in order to maintain the variation piece 54 in linear alignment during its travels.

A first upper band holder 82 is attached to the upper arm 14 proximate the upper top 16 in appropriate fashion while a first lower band holder 84 is attached to the lower arm 24 proximate the lower bottom 28. A resistance band 86 may have a first bulbous end 88 and a second bulbous end 90 and is made from an appropriate resilient material such as rubber. The first end 88 of the band 86 is attached to the first upper band holder 82 while the second end 90 of the band 86 is attached to the first lower band holder 84. The medial portion of the band 86 is received within the channel 60 of the variation piece 54.

In order to use the brace with variable resistance band system 10 of the present invention, the variation piece 54 is attached as described, the brace 12 is moved from its fully flexed configuration to at least partially retract the variation piece 54 and thus hold and secure the variation piece 54 and the brace 12 is attached to a user U in appropriate fashion. A band 86 is selected and has its first end 88 attached to the upper band holder 82 and its second end 90 attached to the lower band holder 84 as described. The user U uses the brace 12 in normal fashion. As the person walks (or uses his or her arm in the case of an elbow brace), the upper arm 14 and lower arm 24 pivot back and forth with respect to each other. As each arm 14 and 24 pivots with respect to the hinge plate 36, the upper gear 42 and the lower gear 48 also pivot in lock step with their respective arm 14 and 24. As the upper gear 42 is gearably meshed with the first set of stem teeth 62 and the lower gear 48 is gearably meshed with the second set of stem teeth 64, the variation piece 54 linearly travels back and forth between an extended and retracted position—as the brace 12 becomes more straightened (arms 14 and 24 at a more obtuse angle with respect to each other), the variation piece 54 retracts and as the brace 12 becomes more flexed (arms 14 and 24 at a more acute angle with respect to each other), the variation piece 54 becomes more extended. As the variation piece 54 becomes more extended (user U bends knee to a greater extent), it presses on the band 86 stretching the band 86 further relative to the stretch imparted by the brace 12 alone, thereby putting more tension on the band 86 and increasing the hamstring loading. If the user U wants more tension or less tension, then the attached band 86 is swapped out for a band meeting the desired tension needs.

The alternate embodiment of the brace with variable resistance band system 110 works in exactly the same fashion, the only difference being the alignment system for the variation piece 154.

If desired, a second upper band holder 92 is attached to the upper arm 14 proximate the upper top 16 and opposite the first upper band holder 82 in appropriate fashion while a second lower band holder 94 is attached to the lower arm 24 proximate the lower bottom 28 opposite the first lower band holder 84. Another band 86 can be attached to these two holders 92 and 94 in order to add quadriceps loading to the brace 12 without the need for the variation piece 54. As with the first band 86, the loading can be changed by changing the band 86 to a band having the desired length and tension level.

The various components of the brace with variable resistance band system 10 and 110, except the band 86 which is made from rubber or similar material, can be made from any appropriate sturdy material such as the same or similar material used to form the arms 14 and 24 of the brace 12, such as hard plastic, etc.

While the invention has been particularly shown and described with reference to an embodiment thereof, it will be appreciated by those skilled in the art that various changes in form and detail may be made without departing from the spirit and scope of the invention.

I claim:
1. A rehabilitation system comprising:
 a brace having an upper arm and a lower arm gearably mated with the upper arm such that rotation of the upper arm causes the lower arm to counter-rotate in lockstep;
 a first gear attached to the upper arm such that the first gear rotates in lockstep with rotation of the upper arm;

a second gear attached to the lower arm such that the second gear rotates in lockstep with rotation of the lower arm;

a variation piece having a head and a stem, the stem having a first set of teeth that mesh with the first gear and a second set of teeth that mesh with the second gear such that rotation of the first gear and the second gear causes the variation piece to linearly travel in a first direction and counter-rotation of the first gear and the second gear causes the variation piece to travel in a second opposing direction; and a first resistance band having a first end attached to the upper arm of the brace and a second end attached to the lower arm and a medial section received by the head of the variation piece.

2. The rehabilitation system as in claim 1 wherein the medial section of the first resistance band is received within a channel located on the head of the variation piece.

3. The rehabilitation system as in claim 1 further comprising alignment means for assisting the variation piece in staying aligned in its linear travel.

4. The rehabilitation system as in claim 1 further comprising a second resistance band having a third end attached to the upper arm of the brace on a side opposite the attachment of the first resistance band and a fourth end attached to the lower arm on a side opposite the attachment of the first resistance band.

5. A rehabilitation system comprising:

a brace having an upper arm pivotally attached to a hinge plate and a lower arm pivotally attached to the hinge plate and the lower arm gearably mated with the upper arm such that rotation of the upper arm causes the lower arm to counter-rotate in lockstep;

a first gear attached to the upper arm such that the first gear rotates in lockstep with rotation of the upper arm;

a second gear attached to the lower arm such that the second gear rotates in lockstep with rotation of the lower arm;

a variation piece having a head and a stem, the stem having a first set of teeth that mesh with the first gear and a second set of teeth that mesh with the second gear such that rotation of the first gear and the second gear causes the variation piece to linearly travel in a first direction and counter-rotation of the first gear and the second gear causes the variation piece to travel in a second opposing direction;

a first resistance band having a first end attached to the upper arm of the brace and a second end attached to the lower arm and a medial section received by the head of the variation piece; and a top plate attached to the hinge plate such that the upper arm, lower arm, first gear and second gear are sandwiched between the top plate and the hinge plate.

6. The rehabilitation system as in claim 5 wherein the medial section of the first resistance band is received within a channel located on the head of the variation piece.

7. The rehabilitation system as in claim 1 further comprising alignment means for assisting the variation piece in staying aligned in its linear travel.

8. The rehabilitation system as in claim 7 wherein the alignment means comprises:

a screw that passes between the top plate and the hinge plate; and a cutaway located on the stem of the variation piece between the first set of teeth and the second set of teeth such that the screw is received within the cutaway.

9. The rehabilitation system as in claim 8 wherein the alignment means further comprises a rail located on the top plate such that at least a portion of the rail is received within the cutaway.

10. The rehabilitation system as in claim 7 wherein the alignment means comprises:

a rail located on the top plate; and a cutaway located on the stem of the variation piece between the first set of teeth and the second set of teeth such that at least a portion of the rail is received within the cutaway.

11. The rehabilitation system as in claim 7 wherein the alignment means comprises:

a rectangular base forming a portion of the stem such that the first set of teeth and second set of teeth sit on the base; and a channel located on the top plate such that at least a portion of the rail is received within the channel.

12. The rehabilitation system as in claim 5 further comprising a second resistance band having a third end attached to the upper arm of the brace on a side opposite the attachment of the first resistance band and a fourth end attached to the lower arm on a side opposite the attachment of the first resistance band.

* * * * *